United States Patent
Spinner et al.

(10) Patent No.: US 8,027,718 B2
(45) Date of Patent: Sep. 27, 2011

(54) REGIONAL ANESTHETIC

(75) Inventors: Robert J. Spinner, Rochester, MN (US);
David P. Martin, Rochester, MN (US);
Timothy R. Conrad, Eden Prairie, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 361 days.

(21) Appl. No.: 11/370,967

(22) Filed: Mar. 7, 2006

(65) Prior Publication Data

US 2007/0213771 A1  Sep. 13, 2007

(51) Int. Cl.
*A61N 1/30* (2006.01)
*A61N 1/00* (2006.01)
(52) U.S. Cl. .............................. 604/20; 607/2
(58) Field of Classification Search ............... 604/272, 604/20, 93.01, 264, 500; 607/2, 46, 47, 63, 607/72
See application file for complete search history.

(56) References Cited

U.S. PATENT DOCUMENTS

| | | | | |
|---|---|---|---|---|
| 3,817,254 A | * | 6/1974 | Maurer | 607/46 |
| 4,055,190 A | * | 10/1977 | Tany | 607/46 |
| 4,155,366 A | * | 5/1979 | Di Mucci | 607/46 |
| 4,289,136 A | * | 9/1981 | Rienzo, Sr. | 607/46 |
| 4,535,777 A | | 8/1985 | Castel | |
| 4,841,973 A | * | 6/1989 | Stecker | 607/58 |
| 5,007,902 A | | 4/1991 | Witt | |
| 5,119,832 A | | 6/1992 | Xavier | |
| 5,188,104 A | | 2/1993 | Wernicke et al. | |
| 5,330,515 A | * | 7/1994 | Rutecki et al. | 607/46 |
| 5,562,717 A | * | 10/1996 | Tippey et al. | 607/41 |
| 5,702,428 A | * | 12/1997 | Tippey et al. | 607/41 |
| 5,792,187 A | | 8/1998 | Adams | |
| 5,995,872 A | * | 11/1999 | Bourgeois | 607/40 |
| 6,002,964 A | | 12/1999 | Feler et al. | |
| 6,027,456 A | | 2/2000 | Feler et al. | |
| 6,035,657 A | | 3/2000 | Dobak, III et al. | |
| 6,104,957 A | | 8/2000 | Alo et al. | |
| 6,167,305 A | | 12/2000 | Cammilli et al. | |
| 6,246,912 B1 | | 6/2001 | Sluijter et al. | |
| 6,298,256 B1 | | 10/2001 | Meyer | |

(Continued)

FOREIGN PATENT DOCUMENTS

GB   2449546 A   11/2008

(Continued)

OTHER PUBLICATIONS

Gainer, et al., "Use of the Peripheral Nerve Stimulator and Standard, Unsheathed Needles in Performing Regional Nerve Blocks", *CRNA: Clinical Forum for Nurse Anesthetists*, 3 (4)186-9 (Nov. 1992).

(Continued)

*Primary Examiner* — Nicholas D Lucchesi
*Assistant Examiner* — Victoria P Campbell
(74) *Attorney, Agent, or Firm* — Perkins Coie LLP

(57) ABSTRACT

A method and apparatus are disclosed for anesthetizing a region of a patient's body. The method includes identifying a target nerve which, upon activation, anesthetizes a region of a patient's body including a surgical site. The target nerve is located and an active site of a nerve blocking apparatus is placed in proximity to the nerve. The nerve blocking apparatus is activated to block neural propagation along the nerve. The activation of the nerve blocking apparatus is maintained during a surgical procedure at the surgical site.

27 Claims, 5 Drawing Sheets

U.S. PATENT DOCUMENTS

| | | | |
|---|---|---|---|
| 6,325,764 B1 | 12/2001 | Griffith et al. | |
| 6,381,496 B1 | 4/2002 | Meadows et al. | |
| 6,393,328 B1 * | 5/2002 | McGraw et al. | 607/72 |
| 6,421,566 B1 | 7/2002 | Holsheimer | |
| 6,487,446 B1 | 11/2002 | Hill et al. | |
| 6,516,227 B1 | 2/2003 | Meadows et al. | |
| 6,684,105 B2 | 1/2004 | Cohen et al. | |
| 6,712,753 B2 | 3/2004 | Manne | |
| 6,754,539 B1 | 6/2004 | Erickson et al. | |
| 6,795,737 B2 | 9/2004 | Gielen et al. | |
| 6,895,280 B2 | 5/2005 | Meadows et al. | |
| 6,928,280 B1 | 8/2005 | Xanthos | |
| 6,928,320 B2 | 8/2005 | King | |
| 6,941,173 B2 * | 9/2005 | Nachum | 607/50 |
| 7,047,079 B2 * | 5/2006 | Erickson | 607/46 |
| 7,117,034 B2 | 10/2006 | Kronberg | |
| 7,177,690 B2 | 2/2007 | Woods et al. | |
| 7,260,436 B2 | 8/2007 | Kilgore et al. | |
| 7,263,402 B2 | 8/2007 | Thacker et al. | |
| 7,337,005 B2 | 2/2008 | Kim et al. | |
| 7,337,006 B2 | 2/2008 | Kim et al. | |
| 7,386,341 B2 | 6/2008 | Hafer | |
| 7,389,145 B2 | 6/2008 | Kilgore et al. | |
| 7,433,734 B2 | 10/2008 | King | |
| 7,502,651 B2 | 3/2009 | Kim et al. | |
| 7,502,652 B2 * | 3/2009 | Gaunt et al. | 607/46 |
| 2002/0055779 A1 | 5/2002 | Andrews | |
| 2004/0049231 A1 | 3/2004 | Hafer | |
| 2004/0073159 A1 | 4/2004 | Nelson | |
| 2004/0127942 A1 | 7/2004 | Yomtov | |
| 2004/0158304 A1 | 8/2004 | Cory et al. | |
| 2004/0167583 A1 | 8/2004 | Knudson et al. | |
| 2004/0172085 A1 | 9/2004 | Knudson et al. | |
| 2004/0172086 A1 | 9/2004 | Knudson et al. | |
| 2004/0172088 A1 | 9/2004 | Knudson et al. | |
| 2004/0176812 A1 | 9/2004 | Knudson et al. | |
| 2005/0038484 A1 | 2/2005 | Knudson et al. | |
| 2005/0060006 A1 | 3/2005 | Pflueger et al. | |
| 2005/0148951 A1 * | 7/2005 | Gonon | 604/264 |
| 2005/0149148 A1 | 7/2005 | King | |
| 2005/0267545 A1 | 12/2005 | Cory | |
| 2006/0025832 A1 | 2/2006 | O'Keeffe et al. | |
| 2006/0030899 A1 | 2/2006 | O'Keeffe et al. | |
| 2006/0041285 A1 * | 2/2006 | Johnson | 607/46 |
| 2006/0184211 A1 * | 8/2006 | Gaunt et al. | 607/48 |
| 2007/0150034 A1 | 6/2007 | Rooney et al. | |
| 2007/0293915 A1 | 12/2007 | Kilgore et al. | |
| 2007/0299482 A1 * | 12/2007 | Littlewood et al. | 607/46 |
| 2008/0058875 A1 | 3/2008 | Greenberg et al. | |
| 2008/0058888 A1 | 3/2008 | King | |
| 2008/0294221 A1 | 11/2008 | Kilgore et al. | |
| 2010/0274326 A1 | 10/2010 | Chitre | |

FOREIGN PATENT DOCUMENTS

| WO | WO 03/011361 A2 | 2/2003 |
|---|---|---|

OTHER PUBLICATIONS

Klein, "Continuous Peripheral Nerve Blocks", *Anesthesiology*, vol. 103, pp. 921-1044 (Nov. 2005).

Capdevila, et al., "Continuous Peripheral Nerve Blocks in Hospital Wards after Orthopedics Surgery", *Anesthesiology*, vol. 103, pp. 1035-1045 (Nov. 2005).

Faccenda, et al., Complications of Regional Anaesthesia Incidence and Prevention, *Drug Safety: An International Journal of Medical Toxicology and Drug Experience*, 24 (6) 413-42 (2001).

"Incredible Save Followed by Poor Communication" *APSF Newsletter*, pp. 63 and 64 (Winter 2005-2006).

Dapoigny et al., "Vagal influence on colonic motor activity in conscious nonhuman primates", *Am. J. Physiol.*, 262: G231-G236 (1992).

Van Den Honert, et al., "Generation of Unidirectionally Propagated Action Potentials in a Peripheral Nerve by Brief Stimuli", *Science*, vol. 206, pp. 1311-1312.

Petrofsky, et al., "Impact of Recruitment Order on Electrode Design for Neural Prosthetics of Skeletal Muscle", *Am. J. of Physical Medicine*, vol. 60, No. 5, pp. 243-253 (1981).

Paterson CA, et al., "Determinants of Occurrence and Volume of Transpyloric Flow During Gastric Emptying of Liquids in Dogs: Importance of Vagal Input", *Dig Dis Sci*, (2000);45:1509-1516.

Solomonow, et al. "Control of Muscle Contractile Force through Indirect High-Frequency Stimulation", *American Journal of Physical Medicine*, vol. 62, No. 2, pp. 71-82 (1983).

Kilgore, et al., "Nerve Conduction Block Utilizing High-Frequency Alternating Current", *Medical and Biological Engineering and Computing*, vol. 24, pp. 394-406 (2004).

Butson, et al., "Role of Electrode Design on the Volume of Tissue Activated During Deep Brain Stimulation", *J. Neural Eng.*, vol. 3, pp. 1-8 (2006).

B. Braun Medical, Inc.; http://www.bbraunusa.com/stimuplex/index.html (p. 2 of specification).

International Search Report for Application No. PCT/US2007/005614; Applicant: Mayo Foundation for Medical Education and Research; Date of Mailing: Aug. 13, 2007 (4 pages).

Bhadra MD, Niloy et al., "High-Frequency Electrical Conduction Block of Mammalian Peripheral Motor Nerve," Muscle & Nerve, Dec. 2005, pp. 782-790, Wiley Periodicals, Inc.

Grill, Warren M. et al., "Stimulus Waveforms for Selective Neural Stimulation," IEEE Engineering in Medicine and Biology, Jul./Aug. 1995, pp. 375-385.

Melzack, Ronald et al., "Pain Mechanisms: A New Theory," Science, vol. 150, No. 3699, Nov. 19, 1965, pp. 971-979.

Shealy MD, C. Norman et al., "Electrical INhibition of Pain by Stimulation of the Dorsal Columns: Preliminary Clinical Report," Anesthesia and Analgesia, vol. 46 No. 4, Jul.-Aug. 1967, 3 pgs.

Bhadra, N. And Kilgore, K.L., "Nerve conduction block utilising high-frequency alternating current," Medical & Biological Engineering & Computing 2004, vol. 24. pp. 394-406.

Gainer et al., "Use of the Peripheral Nerve Stimulator and Standard, Unsheathed Needles in Performing Regional Nerve Blocks," CRNA: The Clinical Forum for Nurse Anesthetists, vol. 3, No. 4, Nov. 1992, 4 pages.

* cited by examiner

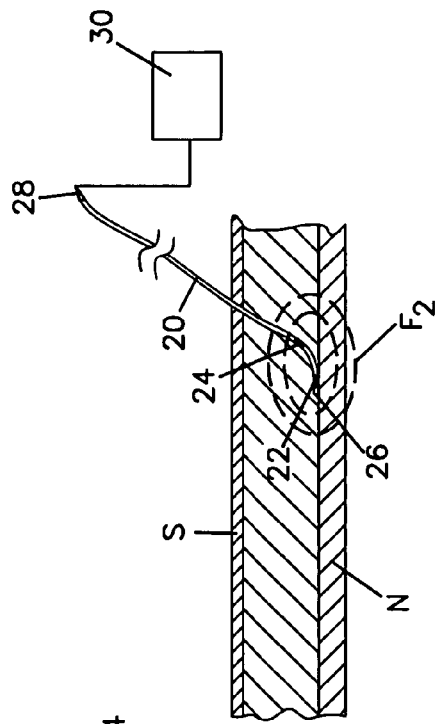
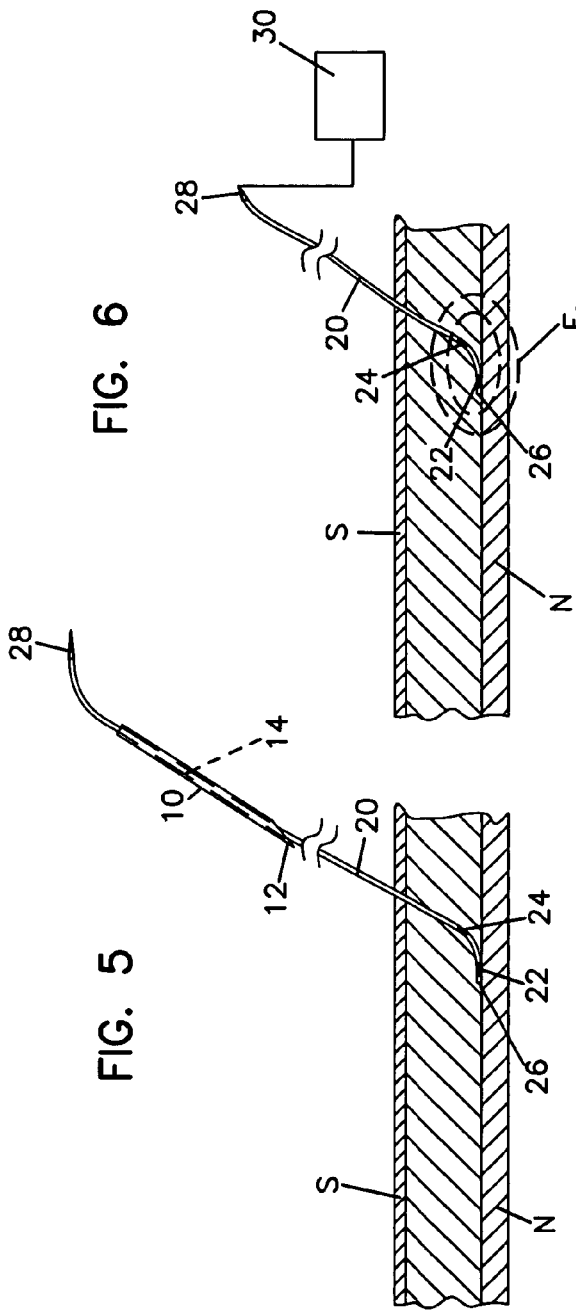
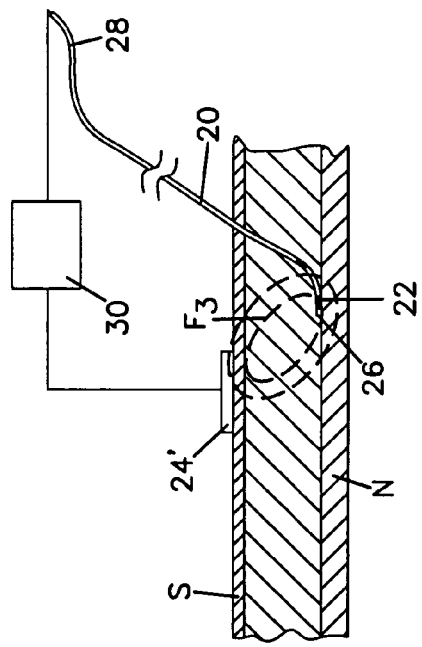

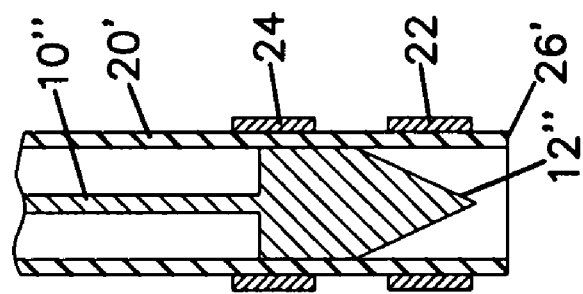
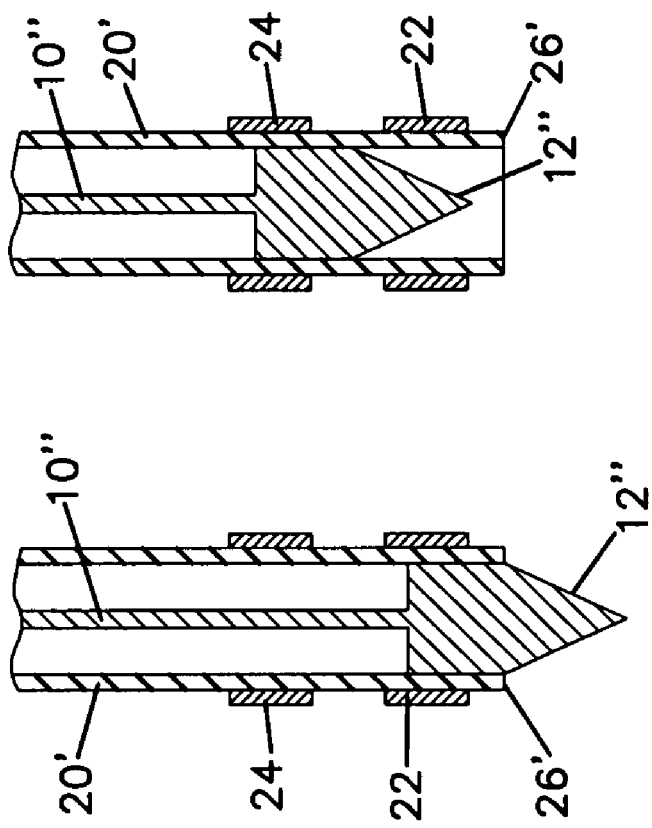
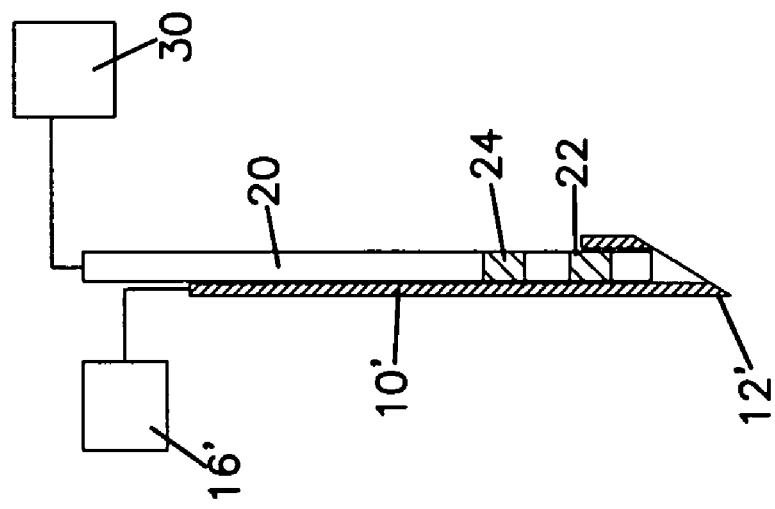

REGIONAL ANESTHETIC

I. BACKGROUND OF THE INVENTION

1. Field of the Invention

This application pertains to method and apparatus for providing an anesthetic to a region of a patient's body.

2. Description of the Prior Art a. Regional Anesthetics

Regional anesthetics are known to be attractive alternatives to general anesthetics for surgical procedures. For example, in knee surgery, it is possible to anesthetize the leg without need for a general anesthetic. Such procedures can enjoy better patient tolerance and faster recovery.

In a typical regional anesthetic procedure, a target nerve is identified for anesthetic treatment. For example, in a knee surgery, the femoral and sciatic nerves are preferred nerves for anesthetic treatment to numb the surgical region. For shoulder surgery, the brachial plexus nerve is the preferred nerve for anesthetic treatment.

With a target nerve identified, an electrically insulated needle with an electrode tip is advanced through the patient's skin and directed toward the suspected location of the nerve. The needle is coupled to a signal generator for creating a stimulating signal at the needle electrode. The physician determines when the needle is near the target nerve by observing a patient response to the stimulus at the needle electrode. For example, when the needle electrode is in close proximity to the sciatic nerve, the patient's foot moves in response to the stimulus. As used herein, "proximity" means close enough to the nerve that the electrical field from the electrode creates a detectable physiologic response in the nerve (i.e., creating neural impulses in the case of a stimulation signal or inhibiting the propagation of neural impulses in the case of a blocking signal as will be described). "Proximity" is a function of a number of variables including amplitude of the signal. A higher current field will electrically couple with a nerve from a greater distance.

When the physician is confident the needle is in close proximity to the target nerve, a local pharmacological anesthetic is delivered to the nerve. Such anesthetic may be injected through the bore of the needle to the target nerve. Alternatively, a catheter may be advanced through the needle bore to the target nerve. The needle is then removed over the catheter leaving the catheter in place at the target nerve. The local anesthetic is passed through the catheter to the target nerve. The catheter may be left in place for several days to permit delivery of anesthetic for an extended period. Such procedures are described in Gainer, et al., "Use of the Peripheral Nerve Stimulator and Standard, Unsheathed Needles in Performing Regional Nerve Blocks", *CRNA: Clinical Forum for Nurse Anesthetists,* 3 (4) 186-9 (November 1992). Such procedures are also described in Klein, "Continuous Peripheral Nerve Blocks", *Anesthesiology*, Vol. 103, pp. 921-1044 (November 2005) and Capdevila, et al., "Continuous Peripheral Nerve Blocks in Hospital Wards after Orthopedics Surgery", *Anesthesiology*, Vol. 103, pp. 1035-1045 (November 2005).

Needles for performing the above-described procedure are commercially available. For example, such needles are available through B. Braun Medical, Inc. The STIMUPLEX® insulated needles come in 20-22 gauge sizes and are used for single injections. The larger CONTIPLEX® 18 gauge needle allows the passage of a 20 gauge catheter for extended pharmacological nerve blocks. Both types of needles attach to the STIMUPLEX® HNS 11 nerve stimulator. Such stimulators generate a stimulation signal at 1 or 2 Hz (switchable) with a maximum current at 5 mA.

Needles for facilitating nerve location during a peripheral nerve block procedure are described in U.S. Pat. No. 6,325,764 to Griffith et al. issued Dec. 4, 2001, U.S. Pat. No. 6,298,256 to Meyer issued Oct. 2, 2001 and U.S. Pat. No. 5,007,902 to Witt issued Apr. 16, 1991 (all incorporated herein by reference). Such needles are also described in U.S. patent application Publication No. 2004/0049231 A1 to Hafer published Mar. 11, 2004, U.S. patent application Publication No. 2004/0158304 to Cory et al. published Aug. 12, 2004 and U.S. patent application Publication No. 2005/0267545 A1 to Cory published Dec. 1, 2005 A1 (all incorporated herein by reference). The '545 application describes a low frequency stimulation (1 to 5 Hz) and a higher frequency background signal (500 to 10000 Hertz) at very low amplitude (less than 100 microamperes) for use in locating a nerve.

While the fore-going regional anesthetic procedure can have advantages over a general anesthetic, the procedure is not without disadvantages. An anesthesiologist finds the nerve through electrical stimulation and then administers the anesthetic. The anesthesiologist waits a period of time (e.g., 30 minutes) to confirm the effectiveness of the anesthetic procedure. This delay interrupts the efficient use of the anesthesiologist's time as well as efficient use of valuable operating room time. If the block is not working after the delay, salvage is problematic and the anesthesiologist usually resorts to a general anesthetic. Further, the procedure requires administration of fluid to a specific site. Such fluid may accumulate and present complications. Also, the procedure is not always effective. For example, the needle may stimulate a nerve but be separated from the nerve by a tissue plane. The administered anesthetic may simply push against the tissue plane and displace the nerve without numbing the nerve. In such cases, the procedure must be repeated or the patient put on a general anesthetic. Complications associated with regional anesthetics are described in Faccenda, et al., "Complications of Regional Anaesthesia Incidence and Prevention, *Drug Safety: An International Journal of Medical Toxicology and Drug Experience,* 24 (6) 413-42 (2001). Toxicity of local anesthetics is described in "Incredible Save Followed By Poor Communication" *APSF Newsletter*, pp. 63 and 64 (Winter 2005-2006) (describing an incidence of accidental delivery of an anesthetic into a vein resulting in cardiac arrest). Further, the volume of the local agent or the delivery needle itself can directly damage a nerve. Complications are also described in the afore-referenced article by Capdevila, et al.

U.S. patent application Publication No. 2006/0025832 A1 published Feb. 2, 2006 and U.S. patent application Publication No. 2006/0030899 A1 published Feb. 9, 2006 describe implantable systems for stimulating peripheral nerves to treat pain. No use of blocking frequencies is disclosed.

The present invention improves the prior art technique by applying alternative nerve blocking techniques to the target nerve.

b. Neural Blocking

Neural stimulation (such as the prior art stimulation noted above to verify placement of a needle in close proximity to a nerve) involves applying a signal to a nerve. The signal parameters (pulse width, frequency and amplitude) are selected to initiate neural action potentials to be propagated along the nerve to a limb (e.g., in the example given above, to cause foot movement).

Not all electrical signals applied to nerves are stimulation signals. Certain parameters can result in a signal that inhibits the nerve or blocks the propagation of action potentials along the nerve.

Many different forms of nerve blocking are known. Cryogenic nerve blocking of the vagus is described in Dapoigny et al., "Vagal influence on colonic motor activity in conscious nonhuman primates", *Am. J. Physiol.*, 262: G231-G236 (1992). Electrically induced nerve blocking is described in Van Den Honert, et al., "Generation of Unidirectionally Propagated Action Potentials in a Peripheral Nerve by Brief Stimuli", *Science*, Vol. 206, pp. 1311-1312. An electrical nerve block is described in Solomonow, et al., "Control of Muscle Contractile Force through Indirect High-Frequency Stimulation", *Am. J. of Physical Medicine*, Vol. 62, No. 2, pp. 71-82 (1983) and Petrofsky, et al., "Impact of Recruitment Order on Electrode Design for Neural Prosthetics of Skeletal Muscle", *Am. J. of Physical Medicine*, Vol. 60, No. 5, pp. 243-253 (1981). A neural prosthesis with an electrical nerve block is also described in U.S. Patent Application Publication No. US 2002/0055779 A1 to Andrews published May 9, 2002. A cryogenic vagal block is described in Paterson C A, et al., "Determinants of Occurrence and Volume of Transpyloric Flow During Gastric Emptying of Liquids in Dogs: Importance of Vagal Input", *Dig Dis Sci*, (2000); 45:1509-1516.

A frequency of a blocking signal is greater than a 200 Hz threshold and, preferably, greater than 500 Hz. Solomonow, et al. "Control of Muscle Contractile Force through Indirect High-Frequency Stimulation", *American Journal of Physical Medicine*, Volume 62, No. 2, pages 71-82 (1983). Higher frequencies of as high as 5,000 Hz result in more consistent neural conduction block. Kilgore, et al., "Nerve Conduction Block Utilizing High-Frequency Alternating Current", *Medical and Biological Engineering and Computing*, Vol. 24, pp. 394-406 (2004).

The nerve conduction block is applied with electrical signals selected to block the entire cross-section of the nerve (for example, both afferent, efferent, myelinated and non-myelinated fibers) at the site of applying the blocking signal (as opposed to selected sub-groups of nerve fibers or just afferent and not efferent or vice versa).

c. Use of Neural Blocking in Treatments

U.S. Pat. No. 5,188,104 to Wernicke et. al. Dated Feb. 23, 1993 describes sub-selection of fibers in a nerve by selecting a treatment frequency by which blocks certain nerve fiber types in the nerve while stimulating other nerve fiber types. Since certain fibers are stimulated while other fibers are blocked, there is no cross-section inhibition or blocking of the entire nerve and all of its nerve fiber types (for example, both afferent, efferent, myelinated and non-myelinated fibers).

U.S. Pat. No. 5,119,832 to Xavier issued Jun. 9, 1992 describes an epidural catheter with nerve stimulators. The '832 patent describes electrical stimulation (with or without concurrent drug treatment) in the epidural space to relieve pain. The electrical stimulation is low frequency (e.g., 0-120 pulses per second) and described as acting almost exclusively on the pain impulse traffic along the type C fibers in the spinal nerves.

U.S. Pat. No. 6,684,105 to Cohen et al. dated Jan. 27, 2004 (assigned to Biocontrol Medical Ltd.) teaches collision blocking in which a stimulation signal is applied to a nerves and an appropriately timed stimulus is applied to nerve to create neural impulses which collide with and thereby block propagation of the stimulation signal in a given direction. No therapy is achieved by the blocking. Such blocking avoids adverse side effects associated with permitting the stimulation signal propagating in an undesired direction to an organ not targeted for therapy.

U.S. patent application Publ. No. 2002/0055779 A1 published May 9, 2002 describes applying a high frequency block to a sciatic nerve to block undesired neural impulses which would otherwise contribute to spastic movement. With such spasm-inducing signals blocked, a therapy signal is applied to the muscle to stimulated desired muscle contractions. U.S. patent application Publ. No. 2005/0149148 A1 published Jul. 7, 29005 (assigned to Medtronic, Inc.) teaches using a blocking signal to avoid undesired side effect (i.e., pain) otherwise associated with a stimulation signal.

The use of a blocking signal as a therapy is described in various patent applications assigned to EnteroMedics, Inc. These applications pertain to use of a conduction block technology to a nerve for a treatment of a variety of gastrointestinal disorders. These applications (incorporated herein by reference) include the following (all filed Sep. 29, 2003): U.S. patent application Ser. No. 10/674,330 (published Sep. 2, 2004 as Publication No. US 2004/0172086 A1); U.S. patent application Ser. No. 10/675,818 (published Sep. 9, 2004 as US Patent Application Publication No. US 2004/0176812 A1) and U.S. patent application Ser. No. 10/674,324 (published Sep. 2, 2004 as US Patent Application Publication No. 2004/0172085 A1). The same assignee is assigned U.S. patent application Ser. Nos. 10/752,994 and 10/752,940 both filed Jan. 6, 2004 with respective publication dates of Aug. 26, 2004 and Sep. 2, 2004, Publication Nos. US 2004/0167583 A1 and 2004/0172088 A1.

d. Accommodation

Blockage of a nerve can result in nerve accommodation in which other nerve groups assume, in whole in part, the function of the blocked nerve. For example, sub-diaphragm blocking of the vagus nerve may be accommodated by the enteric nervous system. U.S. patent application Ser. No. 10/881,045 filed Jun. 30, 2004 (published Feb. 17, 2005 as Publication No. US 2005/0038484 A1) (assigned to EnteroMedics, Inc.) (incorporated herein by reference) notes that a duty cycle of electrical impulses to the nerve to block neural conduction on the nerve can be adjusted between periods of blocking and no blocking in order to vary the amount of down regulation of the vagus nerve as well as preventing accommodation by the enteric nervous system.

II. SUMMARY OF THE INVENTION

A method and apparatus are disclosed for anesthetizing a region of a patient's body. The method includes identifying at least one target nerve which, upon activation, anesthetizes a region of a patient's body including a surgical site. The target nerve is located and an active site of a nerve blocking apparatus is placed in proximity to the nerve. The nerve blocking apparatus may be placed by surgical or percutaneous access or may be placed on the skin for transcutaneous application. The nerve blocking apparatus is activated to block neural propagation along the nerve. The activation of the nerve blocking apparatus is maintained during a surgical procedure at the surgical site. The activation can be maintained for controlling post-operative pain.

III. BRIEF DESCRIPTION OF THE DRAWINGS

FIG. 5 is the view of FIG. 4 with the needle in the process of being withdrawn over the catheter;

FIG. 6 is the view of FIG. 5 with the needle fully withdrawn and with electrodes of the catheter connected to a blocking signal source;

FIG. 7 is the view of FIG. 6 with an alternative embodiment with a return electrode residing of the skin layer;

FIG. 8 is a schematic longitudinal sectional view of an alternative embodiment of the present invention;

FIG. 9 is a longitudinal section view of a still further alternative embodiment of the present invention shown in a first state;

FIG. 10 is the view of FIG. 9 with the apparatus shown in a second state;

IV. DESCRIPTION OF A PREFERRED EMBODIMENT

With reference now to the various drawing figures in which identical elements are identically numbered, preferred embodiments of the present invention will now be described.

Figure 1:
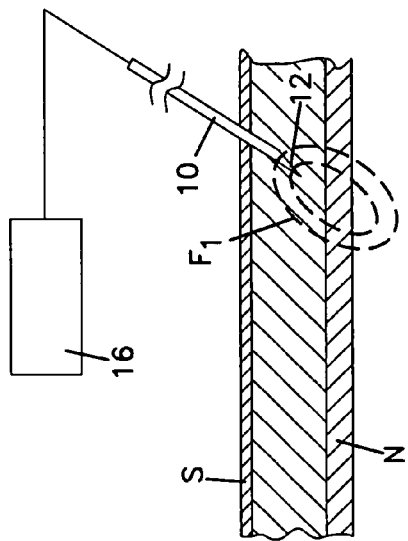
FIG. 1 is a schematic representation of a target nerve beneath a skin layer and with a needle positioned to be advanced through the skin toward the nerve.

FIG. 1 illustrates a needle 10 positioned to be urged through a skin layer S into proximity with a target peripheral nerve N. As used herein, "proximity" means close enough to the nerve that the electrical field from the electrode creates a detectable physiologic response in the nerve (i.e., creating neural impulses in the case of a stimulation signal or inhibiting the propagation of neural impulses in the case of a blocking signal as will be described). "Proximity" is a function of a number of variables including amplitude of the signal. A higher current field will electrically couple with a nerve from a greater distance. Those of ordinary skill in the art will recognize that electrode design and contact geometry will effect the volume of tissue activated during application of a signal. Butson, et al., "Role of Electrode Design on the Volume of Tissue Activated During Deep Brain Stimulation", *J. Neural Eng.*, Vol. 3, pp. 1-8 (2006).

By way of non-limiting example, a patient may be scheduled for a knee surgery. The target nerves are the femoral and sciatic nerves in the thigh of the patient. The needle 10 is preferably an insulated needle with an electrode tip 12 such as the B. Braun Medical, Inc. STIMUPLEX® or CONTIPLEX® needles.

Figure 2:
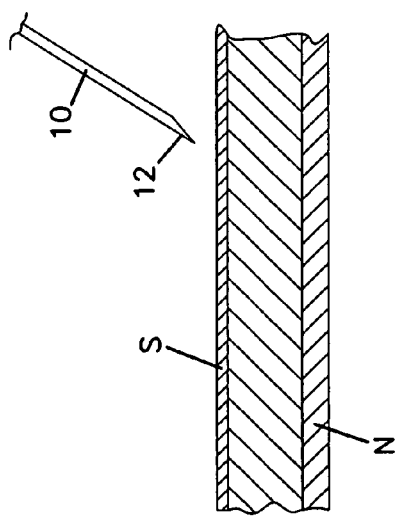
FIG. 2 is the schematic representation of FIG. 1 with the needle advanced to proximity of the nerve sufficient for a stimulation field of the needle to stimulate the nerve.

The needle 10 is connected to a signal generator 16 (FIG. 2) for applying a nerve stimulating signal to the needle 10. Such a signal generator includes the Stimuplex® HNS 11 nerve stimulator.

Proximity of the needle tip 12 to the nerve N is monitored by the physician (e.g., an anesthesiologist). The physician periodically applies a stimulation signal to the electrode tip 12 as the electrode tip 12 is advanced toward the suspected location of the target nerve N. When the needle tip 12 is in close proximity, a field $F_1$ (FIG. 2) created by the stimulating signal creates nerve impulses on the nerve N resulting in an observable physiologic response (such as foot movement).

Figure 3:
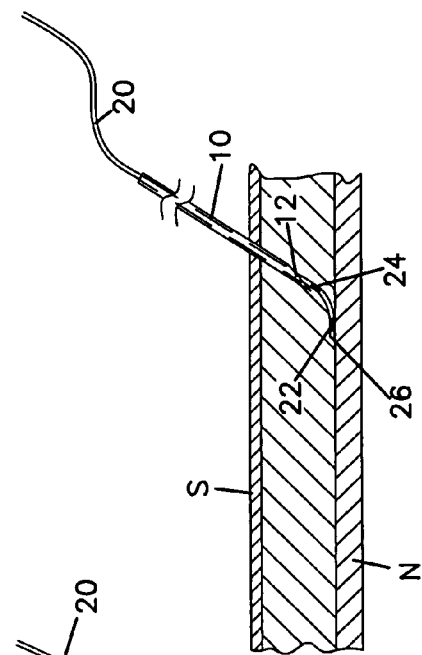
FIG. 3 is the view of FIG. 2 with a catheter with electrodes positioned to be inserted through the needle toward the nerve.
Figure 4:
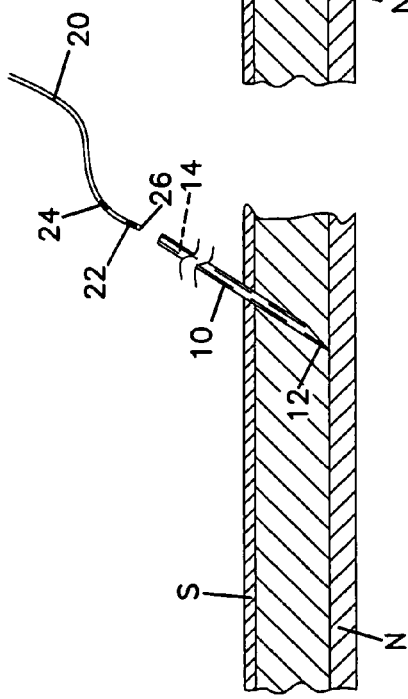
FIG. 4 is the view of FIG. 3 with a distal tip of the catheter advanced through the needle into proximity with the nerve.

Upon observing the physiologic response, the physician advances a catheter 20 through the bore 14 of the needle 10 (FIGS. 3 and 4). The catheter 20 includes an electrode pair 22, 24 near a distal tip 26 of the catheter 20. The catheter 20 is advanced until the distal tip 26 is adjacent the tip 12 of the needle 10. The catheter 20 can have markings along its length to assist the physician in determining the distal tip 26 is at the needle tip 12.

With the catheter 20 advanced to the desired location, the needle 10 is removed by sliding the needle 10 along the length of the catheter 20 and off the proximal end 28 of the catheter (FIG. 5). The proximal end 28 is a pin connector for connection to a blocking signal generator 30. The blocking signal generator generates a waveform selected to block neuronal activity.

The blocking signal can be any electrical signal selected to block neural impulses on a nerve. While the signal can be a direct current signal, a collision block signal or a signal selected to block selected fibers in a nerve bundle (all described above), the signal is preferably a high frequency, bi-phasic signal to block afferent and efferent fibers from propagating nerve impulses at the site of the block. For example, the frequency of the field will have a pulse width selected for the generated field to have a frequency in excess of a 200 Hz threshold as described by Solomonow (article previously described) and, more preferably, 5,000 Hz or higher as described in Kilgore (article previously described). A 5,000 Hz signal will have a pulse width of about 100 microseconds.

Figure 11:
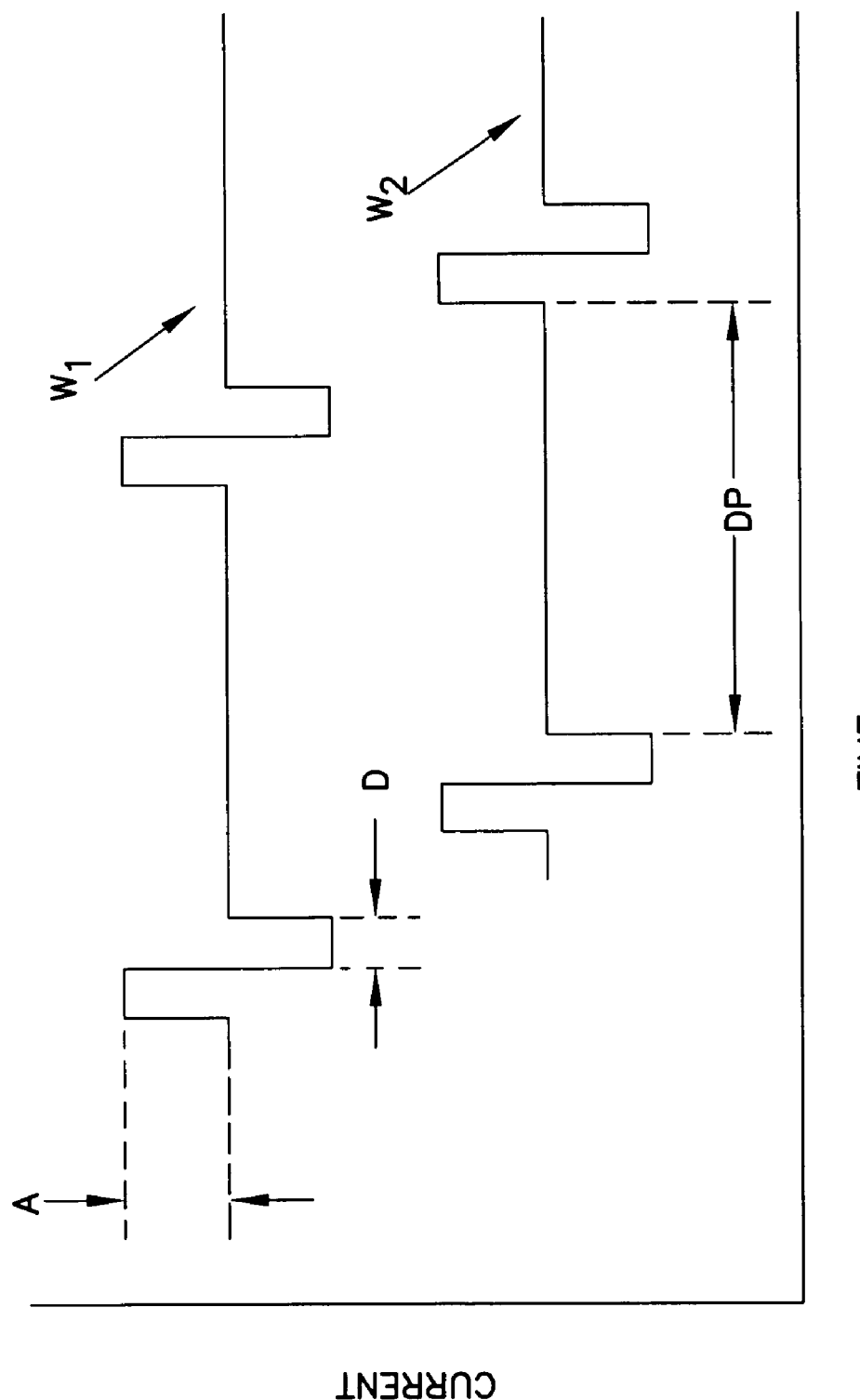
FIG. 11 is a graph illustrating waveforms applied to the electrodes of the apparatus of the present invention.

The electrode pair 22, 24 is a bi-polar electrode pair, which may be provided with a blocking signal as previously described. For example, the electrode 22 may be provided with a first waveform $W_1$ illustrated in FIG. 11. The electrode 24 may be provided with a second waveform $W_2$.

Each of the waveforms $W_1$, $W_2$ is identical differing only in their timing. The waveforms are preferably blocking waveforms having a frequency in excess of a few hundred Hz threshold and more preferably having a frequency of about 2,500 to about 5,000 Hz. At a frequency of 5,000 Hz, the waveforms have a pulse duration D of 100 microseconds. Preferably, each cycle of the waveform has a delayed period DP between the pulses with the duration of the delay period DP equal to two complete cycles (i.e., four pulse durations D or 400 microseconds). The blocking signal is applied at a therapeutic level. For example, the amplitude of the pulse A may be any suitable amplitude to encourage current flow between the electrode pairs and alter a nerve's impulse propagation function. A representative amplitude for such signals would be 0.2 to 8 mA. To drive current across tissue to the nerve N, higher energy levels are anticipated (e.g., voltages up to about 35 volts and currents up to 25 mA).

With the above, the physician can place the catheter 20 as described and apply the blocking signal to create a field $F_2$ on the nerve N. After a short duration (e.g., a few minutes), the physician can confirm the effectiveness of the block by applying a needle or pin test to the desired surgical site to confirm numbness. With such confirmation, the blocking signal is continued and the surgery may proceed.

It is anticipated the blocking signal is applied during patient recovery from surgery. This may last a few days. To avoid displacement of the catheter 20, the catheter is secured to the patient (through tape or the like). If the catheter 20 becomes displaced and the patient senses pain, the placement procedure can be repeated or other anesthesia can be administered.

Advantages of the present invention over the prior art are numerous. They include reduced risk of local anesthetic toxicity and reduced risk of nerve injury. The invention can provide faster onset for operating room throughput and more reliable results. The invention is readily adaptable to existing techniques (such as catheter placement) minimizing training requirements. The invention provides rapid offset for nerve function checks. If a patient has multiple injuries, one area can be repaired and then the function of a downstream area can be checked (e.g. repair a damaged knee and then check foot mobility). Short-acting blocks for outpatient surgery allow for faster discharge from the hospital. The invention can replace lidocaine (or bupivacaine or lignocaine) for spinal anesthesia. Lidocaine can cause transient radicular irritation (i.e., leg pain) when delivered into the spinal column. For military and other applications, the therapy can be applied during transport and may replace morphine in some cases (permitting the patient to remain lucid but with reduced pain). For use in a patient discharged to home, the invention avoids leakage or overdose risks otherwise associated with in-dwelling catheters delivering local anesthetic agents.

FIG. 6 illustrates an embodiment with both electrodes 22, 24 on the catheter 20. Alternatively, one electrode 22 can be on the catheter 20 and a second electrode 24' can be placed on the skin layer S as illustrated in FIG. 7.

The fore going describes a presently preferred embodiment in which a needle 10 (such as the prior art needles described above) is used in a kit with a catheter 20. However, since the needle 10 is not used to deliver a drug, the functions of the needle and catheter can be combined into a single apparatus. Such further embodiments are illustrated in FIGS. 8-10.

In FIG. 8, the catheter 20 with electrodes 22, 24 and blocking generator 30 are substantially as previously described. The needle is replaced with a needle tip 12' with a handle 10'. The needle tip 12' and catheter 20 are simultaneously advanced toward a target nerve. Following placement, the needle tip 12' is withdrawn. The tip 12' can be scored along its length to permit tearing of the needle tip 12' off of the catheter 20. FIG. 8 illustrates the needle tip 12' connected to a stimulation generator 16'. Alternatively, the blocking generator 30 can be switchable between stimulation and blocking signal modes. In such option, the needle tip 12' can be passive (i.e., not generating a stimulation field). In stead, the stimulation field can be applied to either or both of the electrodes 22, 24 which are exposed over the tip 12'.

In the previously described embodiments, the catheter 20 is solid and flexible with leads (not shown) from the electrodes 22, 24 contained with the catheter. FIGS. 9 and 10 illustrate an embodiment of a hollow catheter 20'. Leads from the electrodes 22, 24 can be embedded within the wall thickness of the catheter 20'. A tissue penetrating tip 12" is slidable received within the catheter 20'. In a first position (FIG. 9), the tip 12" protrudes beyond a distal tip 26' of the catheter 20'. In such position, the tip 12" and catheter 20' are simultaneously advanced toward a nerve. The electrodes 22, 24 are connected to a signal generator switchable between stimulation and blocking modes. In the stimulation modes, the electrodes 22, 24 create a stimulation field for detecting proximity to the target nerve. When such positioning is achieved, the tip 12" is retracted into the catheter 201 (FIG. 10) by retracting rod 10". The catheter 20' can then be secured to the patient with the retracted tip 12" presenting no risk of trauma in the event of movement of the catheter 20'. The signal generator is then switched to blocking mode for the electrodes 22, 24 to creating a field on the nerve to block neural impulses.

While an electrical block apparatus is described in a preferred embodiment, other blocking apparatus can be placed on the catheter. For example, the catheter can be provided with a cryogenic distal tip which can be placed as described above. An example of a catheter with a cryogenic probe is disclosed in U.S. Pat. No. 6,035,657 to Dobak, III et al. issued Mar. 14, 2000 (incorporated herein by reference). Also, if desired, a combination of blocking therapies can be applied to the nerve (e.g., electrical block plus drugs) either simultaneously or alternating.

Figure 12:
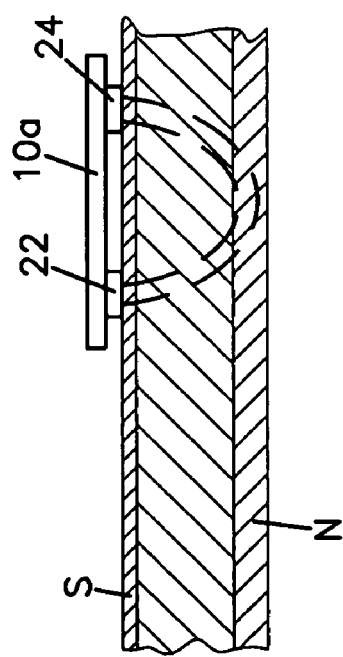
FIG. 12 is the view of FIG. 7 with an alternative embodiment with transcutaneous delivery of a blocking therapy.

While the fore going describes needle delivery of the blocking apparatus, it can also be delivered percutaneously (i.e., through blood vessels) or trancutaneously (across skin). FIG. 12 illustrates a transcutaneous delivery of the therapy where electrodes 22, 24 are provided on a patch 10a placed on the skin S. The electrodes 22, 24 can be switched between stimulation mode (to insure correct placement over the target nerve) and blocking mode with an amplitude selected to generate a field $F_4$ which couples with the nerve N to provide the desired blocking therapy. Such transcutaneous delivery is particularly suitable for nerves near the skin surface such as the sural nerve for knee pain or the ulnar nerve for wrist or hand pain.

Figure 13:
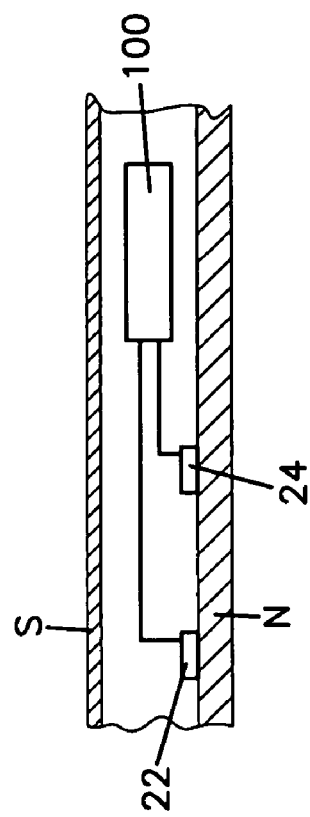
FIG. 13 is the view of FIG. 12 with an alternative embodiment with delivery of a blocking therapy from an implantable pulse generator.

While the preferred embodiment describes use as an anesthesia for surgery, the method and apparatus can be used for treating chronic pain. As illustrated in FIG. 13, the blocking electrodes 22, 24 can be placed near a target nerve N or nerves (either surgically or percutaneously and either along the length of the nerve, as illustrated, or on opposite sides of the nerve) and coupled to an implantable pulse generator 100 (which may include a rechargeable battery) for a source of a blocking signal.

Also, as a modification of the above, an array or plurality of needles and electrodes can be used to simultaneously treat multiple nerves in general location to one another or in different locations (both anatomically different locations or different depth from the skin surface). While the invention is described as treating peripheral nerves, it will be appreciated that the term "nerve" can include nerve roots and nerve fibers throughout the body (e.g., in the spinal column or epidural spaces).

With the foregoing detailed description of the present invention, it has been shown how the objects of the invention have been attained in a preferred manner. Modifications and equivalents of disclosed concepts such as those which might readily occur to one skilled in the art, are intended to be included in the scope of the claims which are appended hereto.

What is claimed is:

1. A method of anesthetizing a region of a patient's body, comprising:
   identifying a target nerve which, upon anesthetization, anesthetizes a region of a patient's body including a surgical site;
   locating the target nerve;
   placing an electrode of a nerve blocking apparatus in proximity to the nerve;
   connecting the electrode to an external power source via a conductive path inserted through the patient's skin;
   anesthetizing the region of the patient's body by activating the electrode at a frequency of at least 5,000 Hz to block neural propagation of afferent pain signals along the nerve; and
   retaining the activated electrode of the nerve blocking apparatus in proximity to the nerve during a surgical procedure at the site.

2. The method of claim 1 wherein activating the electrode includes creating a field near the desired target location with parameters selected to at least partially block neural activity within the field.

3. The method of claim 1 wherein locating the target nerve includes activating an electrical stimulation at a suspected location of the nerve and observing a physiologic response to the stimulation confirming the suspected location.

4. The method of claim 3 wherein locating the target nerve includes placing a needle through a skin of the patient with the electrode positioned on the needle and advanced to the suspected location, and activating the electrode with a stimulation signal selected to induce action potentials in a nerve in close proximity to the electrode.

5. The method of claim 1, further comprising advancing the electrode through a needle to the nerve and connecting the electrode to a source of a nerve blocking signal.

6. The method of claim 5, further comprising withdrawing the needle while leaving the electrode at the nerve.

7. The method of claim 1 wherein the electrode is carried by a catheter having a deployable, tissue-penetrating tip, and wherein placing the electrode includes advancing the catheter through the patient's tissue while the tip projects from the catheter, and withdrawing the tip into the catheter after penetrating through the patient's tissue.

8. The method of claim 7 wherein locating the target nerve includes activating the electrode in accordance with a first mode to stimulate adjacent tissue, and wherein anesthetizing the region of the patient's body includes activating the electrode in accordance with a second mode different than the first mode.

9. The method of claim 1 wherein placing an electrode includes delivering the electrode percutaneously.

10. A method for treating a patient, comprising:
identifying a target nerve which, upon anesthetization, anesthetizes a region of a patient's body including a surgical site;
locating the target nerve;
placing an electrode of a nerve blocking apparatus in proximity to the nerve;
connecting the electrode to an external power source via a conductive path inserted through the patient's skin;
anesthetizing the region of the patient's body by activating the electrode at a frequency of at least 5,000 Hz to block neural propagation of afferent pain signals along the nerve;
retaining the activated electrode of the nerve blocking apparatus in proximity to the nerve during a surgical procedure at the surgical site; and
blocking neural propagation of afferent pain signals after the surgical procedure by activating the electrode at a frequency of at least 5,000 Hz after the surgical procedure.

11. The method of claim 10 wherein blocking neural propagation of afferent pain signals after the surgical procedure includes blocking the pain signals during patient recovery from surgery.

12. The method of claim 10 wherein blocking neural propagation of afferent pain signals after the surgical procedure includes blocking the pain signals to treat chronic patient pain.

13. The method of claim 10 wherein placing an electrode includes delivering the electrode percutaneously.

14. The method of claim 10 wherein placing an electrode includes placing the active electrode surgically.

15. The method of claim 10 wherein anesthetizing the region of the patient's body includes anesthetizing the region during knee surgery.

16. The method of claim 10 wherein blocking neural propagation of afferent pain signals after the surgical procedure includes blocking neural propagation of afferent pain signals for days after the surgical procedure.

17. The method of claim 10, further comprising:
implanting a pulse generator; and
coupling the pulse generator to the electrode.

18. A method for treating a patient, comprising:
identifying a target nerve which, upon anesthetization, anesthetizes a region of a patient's body including a surgical site;
locating the target nerve;
placing an electrode of a nerve blocking apparatus in proximity to the nerve;
connecting the electrode to an external power source via a conductive path inserted through the patient's skin;
anesthetizing the region of the patient's body by activating the electrode at a frequency of at least 5,000 Hz to block neural propagation of afferent pain signals along the nerve;
retaining the activated electrode of the nerve blocking apparatus in proximity to the nerve during a surgical procedure at the surgical site; and
blocking neural propagation of afferent pain signals after the surgical procedure by activating an electrode of the nerve blocking apparatus at a frequency of at least 5,000 Hz after the surgical procedure to treat chronic pain experienced by the patient.

19. The method of claim 18 wherein the nerve blocking apparatus includes multiple electrodes, and wherein activating the electrode in proximity to the nerve includes activating a first electrode, and wherein activating an electrode after the surgical procedure to treat chronic pain experienced by the patient includes activating a second electrode.

20. The method of claim 19 wherein at least one of the electrodes is positioned at the patient's spinal column.

21. The method of claim 19 wherein at least one of the electrodes is positioned in the patient's epidural space.

22. The method of claim 19, further comprising:
implanting a pulse generator; and
coupling the pulse generator to the second electrode.

23. The method of claim 18 wherein placing an electrode includes delivering the electrode percutaneously.

24. The method of claim 18 wherein placing an electrode includes placing the electrode surgically.

25. The method of claim 18 wherein anesthetizing the region of the patient's body includes anesthetizing the region during knee surgery.

26. The method of claim 18 wherein blocking neural propagation of afferent pain signals after the surgical procedure includes blocking neural propagation of afferent pain signals for days after the surgical procedure.

27. The method of claim 18, further comprising:
implanting a pulse generator; and
coupling the pulse generator to the electrode.

* * * * *